(12) United States Patent
Frost

(10) Patent No.: US 6,993,978 B2
(45) Date of Patent: Feb. 7, 2006

(54) PIN DETECTION SYSTEM

(75) Inventor: Charles C. Frost, Ada, MI (US)

(73) Assignee: Frost Links, Inc., Grand Rapids, MI (US)

( * ) Notice: Subject to any disclaimer, the term of this patent is extended or adjusted under 35 U.S.C. 154(b) by 0 days.

(21) Appl. No.: 11/074,461

(22) Filed: Mar. 8, 2005

(65) Prior Publication Data

US 2005/0150308 A1 Jul. 14, 2005

Related U.S. Application Data

(62) Division of application No. 10/356,063, filed on Jan. 31, 2003, now Pat. No. 6,862,939.

(60) Provisional application No. 60/353,679, filed on Jan. 31, 2002.

(51) Int. Cl.
*G01N 3/08* (2006.01)

(52) U.S. Cl. .................................................... 73/828

(58) Field of Classification Search ................ 73/826, 73/827, 828, 831, 862.453, 862.393
See application file for complete search history.

(56) References Cited

U.S. PATENT DOCUMENTS

| | | | |
|---|---|---|---|
| 2,293,578 A | 8/1942 | Tuhy ............................ 184/15 |
| 2,593,841 A | 4/1952 | Burchsted .................... 184/15 |
| 3,998,317 A * | 12/1976 | Stinnett .................. 198/810.02 |
| 4,009,764 A | 3/1977 | Hafner ...................... 184/15 A |
| 4,064,970 A | 12/1977 | Reeves ..................... 184/15 B |
| 4,085,821 A | 4/1978 | Kast et al. ................. 184/15 A |
| 4,151,652 A | 5/1979 | Palma ........................ 33/679.1 |
| 4,212,372 A | 7/1980 | Murphy et al. ........... 184/15 B |
| 4,413,513 A | 11/1983 | Ross et al. ..................... 73/162 |
| 4,506,763 A | 3/1985 | Frost et al. ................. 184/15.2 |
| 4,537,285 A | 8/1985 | Brown et al. .............. 184/15.2 |
| 4,630,712 A | 12/1986 | Hoseley ..................... 184/15.3 |
| 4,871,344 A * | 10/1989 | Morisawa ................... 474/206 |
| 4,877,111 A | 10/1989 | Kilper ........................ 184/15.1 |
| 5,186,280 A | 2/1993 | Mattcheck .................. 184/15.3 |
| 5,365,765 A | 11/1994 | Gohl et al. ................. 72/355.6 |
| 5,378,205 A | 1/1995 | Gohl et al. .................. 474/206 |
| 5,482,154 A | 1/1996 | Affeldt et al. ......... 198/370.04 |
| 5,490,590 A | 2/1996 | Courtney ................. 198/502.4 |
| 5,492,215 A | 2/1996 | Affeldt et al. ........... 198/464.4 |
| 5,563,392 A | 10/1996 | Brown et al. .............. 235/91 R |
| 5,711,050 A | 1/1998 | Pimentel ...................... 15/302 |
| 6,419,078 B1 | 7/2002 | Leathers ..................... 198/500 |

* cited by examiner

*Primary Examiner*—Max Noori
(74) *Attorney, Agent, or Firm*—Van Dyke, Gardner, Linn & Burkhart, LLP

(57) ABSTRACT

A pin detection system and/or method for detecting a pin or bolt in a section of chain comprises a chain or section of chain having a plurality of chain links connected together by a plurality of pins or bolts or the like. At least one end of at least one of the pins or bolts may have an extension extending longitudinally therefrom. A sensor or detector is provided along a conveying path of the chain for sensing the presence of the pin or bolt and/or extension as the section of chain is conveyed along the conveying path. The sensor provides a signal indicative of a detection of the pin or bolt or extension. A control may control at least one accessory associated with the conveyor system in response to a signal generated by the sensor.

16 Claims, 2 Drawing Sheets

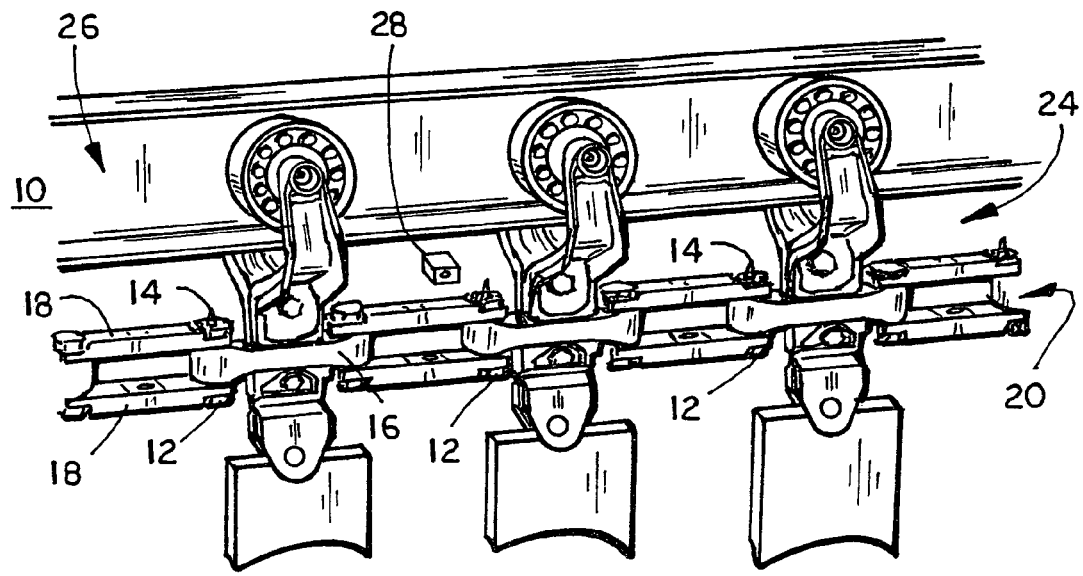
FIG. 1
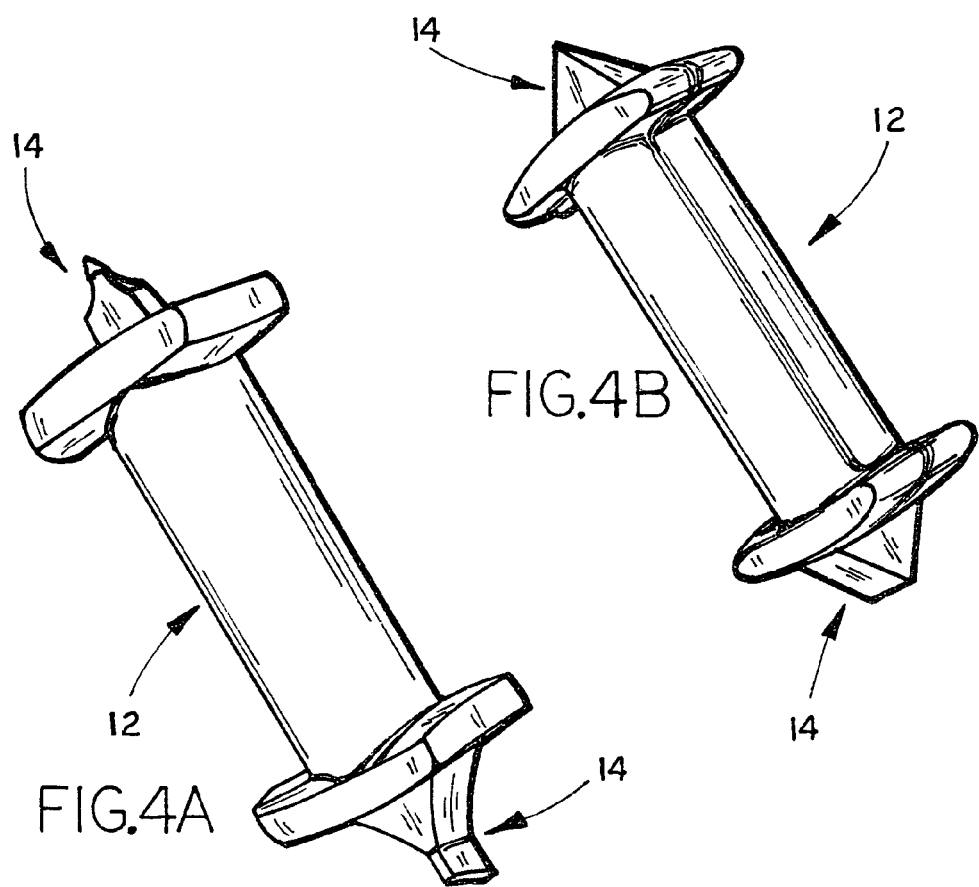
FIG. 4A
FIG. 4B

PIN DETECTION SYSTEM

CROSS REFERENCE TO RELATED APPLICATIONS

The present application is a division of U.S. patent application Ser. No. 10/356,063, filed Jan. 31, 2003, now U.S. Pat. No. 6,862,939, which claims priority of U.S. provisional application Ser. No. 60/353,679, filed Jan. 31, 2002, which are hereby incorporated herein by reference in their entireties.

FIELD OF THE INVENTION

The present invention relates generally to conveyor chains and, more particularly, to methods and/or systems for estimating or determining an amount of wear of the chain links and/or pins or bolts of a conveyor chain or section of chain.

BACKGROUND OF THE INVENTION

Conveyor chains are known in the art and include a plurality of link pins which connect a plurality of center links and side links to form a continuous conveyor chain for conveying conveyor trolleys or the like along a conveying path. As the chain is moved along the conveying path, the links and sections of the chain undergo bends and turns along a continuous conveying path or chain loop. As a section of chain bends, the pins may rotate within the openings in the center links and/or side links, which results in wear on both the pins and the center links and/or side links. The wear leads to an increase in the effective length of the chain or section of chain as well as a change in the pitch of the chain as gaps then may occur between the pins and links. It is generally undesirable to allow excessive wear in the chain, since this results in slack in the chain and/or a change in chain pitch and/or a change in the distance between products being processed, or may further result in noise and further wear or weakening of the chain. Typically, when the wear results in an increase in length of approximately 4–6 inches in a length of a 10-foot section of chain, the chain must be replaced.

Typically, the length of a chain or section of chain is measured between the ends of the center links of successive sections of chain. The length of a section of chain may be determined by detecting the leading ends of consecutive center links and knowing the speed of the chain along the conveying path. The speed of the chain and the time between detections may then be used to calculate the distance or length of the section of chain. This length may be monitored to approximate the wear in the pins and/or links of the sections of chain. However, the center links are typically forged members and may have variable lengths due to the manufacturing tolerances of the center links and surface irregularities of the links. This may result in a high variability in the measured length of the chain links or sections of chain.

Therefore, there is a need in the art for an improved system for monitoring or determining the wear of sections of chain which overcomes the shortcomings of the prior art systems or devices.

SUMMARY OF THE INVENTION

The present invention is intended to provide a pin detecting system or wear measurement system or device which is operable to detect the presence of a pin or pins of a section of chain and to determine a substantially accurate estimate of the degree of wear in the chain links or pins of the section or sections of chain. The wear measurement system may be operable to detect an extension or end of at least one pin, such as an I-pin or bolt or the like, of a respective section of chain and may determine the degree of wear in response to one or more such detections.

According to an aspect of the present invention, a pin detecting system comprises at least one sensor and a plurality of pins connecting side and center links of a section of chain. The pin detecting system is operable to detect at least one of the pins of the section of chain as the chain is conveyed along a conveying path of a conveyor system. At least one of pins may have an extension extending longitudinally from at least one end of the pin. The sensor is positioned along the conveying path and is operable to detect the extension as the extension is conveyed along the conveying path. The sensor generates a signal indicative of the detection of the extension.

The sensor may communicate the signal to a control. The control may be operable to determine an amount or degree of wear in the links and pins of the section of chain in response to the signal or signals from the sensor and the speed of the chain. Optionally, the control may activate or deactivate a chain lubricating device or may control the chain drive motor or device of the conveyor in response to the signal or signals from the sensor.

According to another aspect of the present invention, a chain wear measurement system for determining an amount of wear in at least one section of chain comprises a sensor and a chain having a plurality of links connected together by a plurality of pins. At least one end of at least one of the pins has an extension extending longitudinally therefrom. The sensor is operable to sense or detect the extension as the chain and the extension are conveyed or moved along a conveying path. The sensor generates a signal indicative of a detection of at least one extension. A control may be responsive to the signal from the sensor to determine the degree of wear in the section of chain.

Preferably, the extension extends longitudinally along a center axis of the pin and comprises a generally pointed end.

According to another aspect of the present invention, a method for determining a degree of wear in at least one of a pin or pins and the chain links of a section of chain of a conveyor system comprises providing a chain having a plurality of chain links connected together via a plurality of pins. A detector is provided along a conveying path of the conveyor system for detecting an end of at least one of the pins as the pins are conveyed along the conveying path. An amount of wear in at least one of the chain links and the pins is determined in response to a signal from the detector indicative of a detection of the end of the pin or pins.

Therefore, the present invention provides a pin detection system or wear measurement device or system which is operable to detect a pin or pins of a section of chain and may substantially accurately determine a degree of wear in the pin or pins and/or chain links of the section of chain in response to the detection of the pin or pins. The pins may have a generally pointed extension extending longitudinally from at least one end of the pin or pins for enhanced detection of the pin or pins as the section of chain is conveyed along a conveying path. By detecting the presence of the end of the pin generally along a longitudinal axis of the pin, the present invention provides a substantially accurate determination or estimation of the location of the pin which may not be affected by a variance in the tolerances of the pin itself. Also, by detecting the presence of the end of the pins, the present invention may provide a substantially accurate determination of the degree of wear in a section of chain which may not be affected by variances in the manufacturing tolerances and dimensions and surface irregularities of the chain links of the section of chain. The present invention thus provides a substantially accurate and true determination of the location of the pin or pins of the section of chain and thus may provide a substantially accurate and true determination of the degree of wear in the pins and/or chain links of the section of chain.

These and other objects, advantages, purposes and features of the present invention will become apparent upon review of the following description in conjunction with the drawings.

BRIEF DESCRIPTION OF THE DRAWINGS

FIG. 1 is a perspective view of a pin detecting system or wear measurement system of the present invention, showing a section of a chain connecting trolleys of a conveyor system;

FIG. 4A is a perspective view of a smooth link I-pin in accordance with the present invention, showing optional end extensions; and FIG. 4B is a perspective view of a forged I-pin in accordance with the present invention, showing optional end extensions.

DESCRIPTION OF THE PREFERRED EMBODIMENTS

Figure 2A:
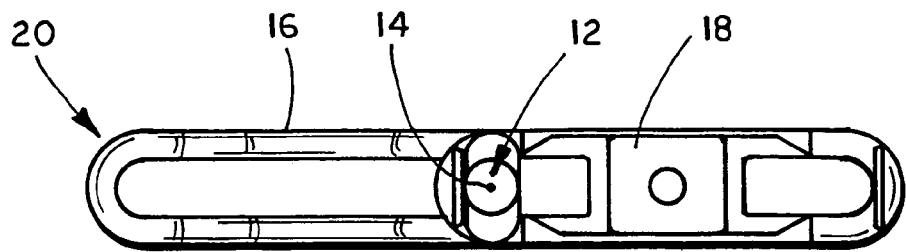
FIG. 2A is a plan view of a section of chain with a pin according to the present invention.

Referring now to the drawings and the illustrative embodiments depicted therein, a pin locating or detecting system or chain wear deduction or measurement device or system 10 includes a pin or pins 12 having an extension 14 extending or projecting from at least one end of at least some of the pins 12 (FIGS. 1–3). Pins 12 connect center links 16 and side links 18 together to form a section or sections of a chain 20, such as in a known manner. Chain wear deduction system 10 includes at least one detector or sensor or trip device 28 for detecting or sensing the pins as the section of chain is conveyed along a conveying path 26. Sensor 28 is provided to detect the raised extension 14 as the section of chain is conveyed past the sensor. The sensor is cooperatively incorporated with a wear monitor system or control (shown generally at 30 in FIG. 1), which may determine the amount of wear in the chain or section of chain in response to the detection of consecutive or spaced raised extensions of the pins of the section or sections of chain. The system may be operable to detect, or respond to the detection of, the raised extensions 14 at each pin, or at every other pin, or at approximately every 10 feet of chain section, or at any other desired increment of pins or chain sections or distance or length, in order to determine a change in the actual pitch of the chain or section of chain as the chain is moved or conveyed along the conveying path and past the sensor or sensors. The length of the chain or section of chain may be determined or calculated in response to the detection of consecutive or spaced extensions or pins and in response to the speed of the chain, which may be input or entered or otherwise known to the control or monitoring system.

Figure 3A:
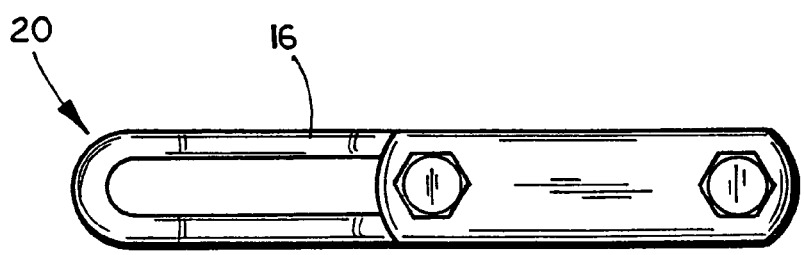
FIG. 3A is a plan view of a bolted chain section having a bolt in accordance with the present invention.
Figures 3B, 3C:
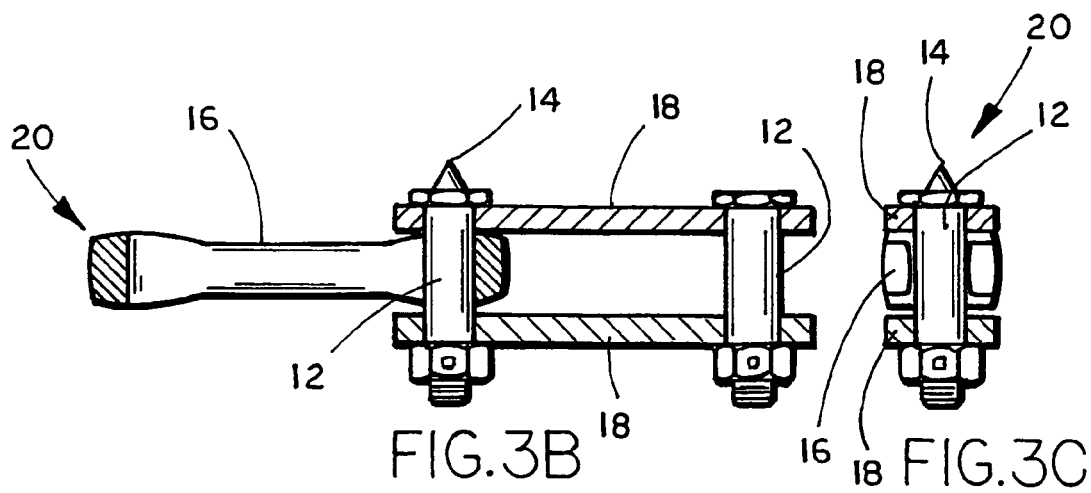
FIG. 3B is a side elevation and partial sectional view of the bolted chain section and bolt of FIG. 3A.
FIG. 3C is an end elevation and partial sectional view of the bolted chain section and bolt of FIGS. 3A and 3B.

The pins 12 of the section of chain 20 may comprise smooth link pins (such as shown in FIG. 4A), such as the types disclosed in U.S. Pat. Nos. 5,365,765 and 5,378,205, the disclosures of which are hereby incorporated with herein by reference, forged I-pins (such as shown in FIG. 4B), or bolts (such as shown in FIGS. 3A–C) or other pins or the like for connecting the chain links 16, 18 and sections of chain together. Each pin 12 connects a center link to a pair of side links to form the continuous chain, as is known in the art. Chain 20 may be connected to a trolley or conveyor 24, such as a Frost Sani-Trolley manufactured by Frost Inc. of Grand Rapids, Mich., or the like to convey products around the conveying path 26 of the conveyor system.

Because the center links and side links of chains are typically forged links, the high variability of the lengths or dimensions or surface impurities or irregularities of the links may lead to a corresponding high variability of the measurements by conventional monitoring systems, which typically measure or monitor the chain at or between the ends of the center links along the chain or section of chain. By positioning and detecting the extensions at the ends of the pins, the present invention is not substantially influenced by the manufacturing tolerances of the center and/or side links. The wear measurement device or system of the present invention may be especially applicable to smooth link pins (such as shown FIG. 4A), due to the tighter tolerance of control during typical manufacturing of such pins. However, the present invention may be applicable to other types of pins, such as forged I-pins (such as shown FIG. 4B), bolts 12' (such as shown in FIGS. 3A–C) or the like, without affecting the scope of the present invention.

Figure 2B:
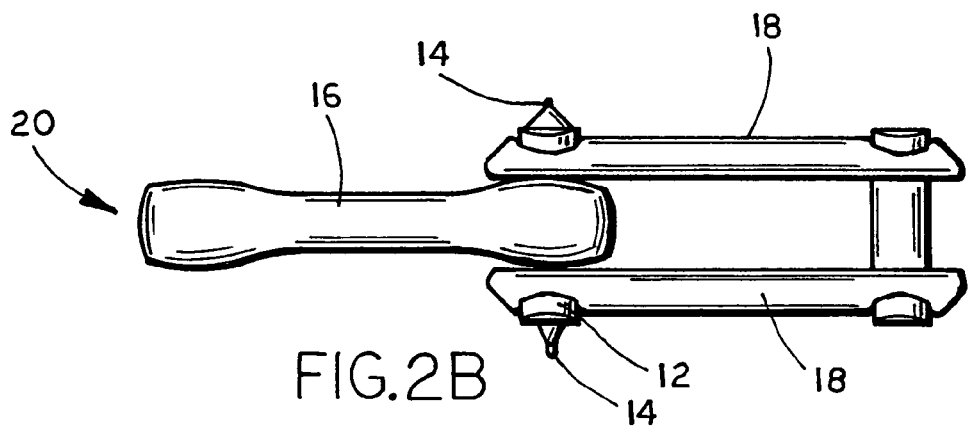
FIG. 2B is a side elevation of the section of chain and pin of FIG. 2A.

Extensions 14 may extend or project from one or both ends of the pin or pins 12 of the chain, preferably generally along a longitudinal axis of the pin so as to minimize variation in the location of the extension as the pin rotates within the joint of the chain. Extensions 14 may be generally conical-shaped (such as shown in FIGS. 2A and 2B), generally cylindrical or conical-shaped and narrowed to a generally pointed end or nipple (such as shown at 14a in FIG. 4A), generally pyramid-shaped (such as shown at 14b in FIG. 4B), generally wedge-shaped (such as shown at 14c in FIG. 4B) or the like, or may have a generally pointed extension or tip extending or protruding from a generally pyramid-shaped or wedge-shaped base (such as shown at 14d in FIG. 4A) or the like. However, other shapes may be implemented at one or both ends of the pins 12, without affecting the scope of the present invention. Preferably, the extensions 14 are formed to narrow to a generally pointed tip at the outer end thereof, in order to minimize the effect of dirt build up on the extensions 14.

Optionally, a bolt 12' may include an extension 14 extending longitudinally from a head portion 13a of bolt 12' (as shown in FIGS. 3A–C), or may include an extension (not shown) extending longitudinally from a fastener end or threaded end 13b of bolt 12', without affecting the scope of the present invention. The extension from the bolt or any other type of pin may comprise one of the shapes shown in FIGS. 1–4 and/or described above, or may comprise any other shape to facilitate detection of the pin or bolt, preferably generally along the longitudinal axis of the pin or bolt, as the chain progresses along the conveying path, without affecting the scope of the present invention.

Sensor or sensors 28 is/are positioned along the conveying path 26 and directed toward or placed at the area or region where the ends of the pins of the chain will pass as the chain is conveyed or moved along the conveying path. Sensor 28 may comprise an optical sensor or photo sensor or the like and is operable to detect extension 14 as it passes by sensor 28. Optionally, sensor 28 may comprise a mechanical trip or trigger device which contacts the extension or extensions 14 as they pass by the sensor, whereby the extension contacts and moves a portion of the sensor, without affecting the scope of the present invention. Sensor 28 generates a signal to control 30 in response to such detection or contact or movement and may be in communication, such as in electrical communication or the like, with the control or monitoring system 30 to communicate the signal thereto. Control 30 may then be operable to determine the amount of wear in the section of chain (or in one or more of the center and/or side links of the section of chain) in response to the detection of the pin or extension or detection of consecutive or spaced pins or extensions by sensor 28. The control may also receive an input or entered value indicative of the speed of the chain and may calculate the length or distance between the detected pins accordingly.

Wear measurement system 10 may be operable to detect (or the control may be responsive to the detection of) the raised extension 14 at each link of the chain, or at approximately every ten feet of chain section, or at any other desired increment of pins or chain sections or distances or lengths, in order to determine a change in the actual pitch of the chain or section of chain as the chain is conveyed past the sensor. Although described as detecting certain increments or lengths of chain, the sensor of the wear measurement system may detect each pin of the chain and communicate a signal indicative of each such detection, while the control may be selectably responsive to only some of the signals, such as every other detection or signal or every third or fourth signal or each signal indicative of every ten feet of chain section or the like, to determine the wear in the chain or section of chain, without affecting the scope of the present invention.

Optionally, the wear measurement system may determine the length of each portion of chain or set of center links and side links by detecting one of the pins of each portion of chain (or being responsive to the detection of one of the pins of each portion of chain), such as the pin at the leading end of each center link or the like. The consecutive signals from the sensor or every other signal from the sensor may then indicate detection of a pin at the leading end of consecutive center links as the section of chain is conveyed along the conveying path. For such an application, every other pin of the section of chain may have an extension (such that the sensor may only detect every other pin of the section of chain), or the control may only process or respond to every other signal from the sensor (if the sensor detects each pin of the section of chain).

Accordingly, wear measurement device or system 10 is operable to detect and determine the location of a pin or pins of a section or sections of chain as the chain is conveyed along the conveying path. The wear measurement system may be operable to measure or determine or approximate the actual pitch of the chain as the chain travels along the conveying path 26 and past the sensor or sensors 28 to determine an increase in chain length and/or chain pitch and thus to determine or monitor the amount of wear on the pins and/or links of the chain or section of chain. The wear measurement or monitoring system 10 thus may monitor the chain or section of chain to determine an increase in chain length or pitch and may thus determine when there is excessive wear in the chain or in one or more sections of chain, whereby the chain or section of chain may need to be replaced. The wear measurement device or system of the present invention thus provides a highly accurate wear measurement system or device and is not dependent on the low manufacturing tolerances and surface irregularities of the center links and/or side links of the chain or section of chain.

It is further envisioned that the sensor of the present invention may be operable to provide a signal or signals to other controls or systems or accessories at desired increments of pins along the chain, or that the control may be operable to perform other functions or to control other accessories, in response to the signal or signals from the sensor. For example, the system or control may provide a signal to activate or deactivate a chain lubricator to lubricate the joints of the chain as the chain joints move past the lubricator, such as in response to signals indicative of detection of each pin or every second, third, or fourth pin or any other increment of pins or chain sections at the sensor. The chain lubricator may comprise any known type of lubricator or lubricating device, or may be of the type disclosed in U.S. Pat. No. 6,419,078, or in International Publication No. WO/00-20307, published Apr. 13, 2000, for LUBRICATING DEVICE FOR CONVEYOR SYSTEMS, the disclosures of which are hereby incorporated herein by reference, without affecting the scope of the present invention. Optionally, the system or control may provide other signals or control functions, such as a signal for controlling the conveyance of the chain, such as for starting or stopping conveyance or movement of the chain at a particular point or location along the conveying path, or adjusting a speed of conveyance or the like, in response to the sensor. Optionally, the control or system may generate one or more other signals to adjust or control a process or system or device or accessory which may be dependent on the amount of travel of the chain along the conveying path, without affecting the scope of the present invention.

Therefore, the pin detection and/or wear measurement system of the present invention provides for detection of a pin or pins of a chain or section of chain as the chain is conveyed along a conveying path. The wear measurement system may provide an accurate and substantially true measure of the pitch of the chain or section of chain which may not be as influenced by the manufacturing tolerances of the chain links or pins as conventional monitoring systems. The present invention thus provides an improved system or method for determining or deducing the amount of wear occurring in a chain or section of chain or sections of chain and is operable to determine such wear while the chain is being driven or conveyed or moved along the conveying path of a conveyor system. Additionally, the present invention provides a chain wear measurement device or system which may not be influenced by dirt build-up on the pins and links of the chain.

Changes and modifications in the specifically described embodiments can be carried out without departing from the principles of the present invention, which is intended to be limited only by the scope of the appended claims, as interpreted according to the principles of patent law including the doctrine of equivalents.

The embodiments of the invention in which an exclusive property or privilege is claimed are defined as follows:

1. A pin detecting system operable to detect a presence of at least one pin of a section of chain as the chain is conveyed along a conveying path of a conveying system, said pin detecting system comprising:

a plurality of pins connecting side links and center links of the section of chain, at least one of said pins having an extension extending longitudinally from at least one end of said at least one of said pins; and at least one sensor positioned along the conveying path and operable to detect said extension of said at least one of said pins as said extension is conveyed along the conveying path, said at least one sensor generating a signal indicative of the detection of said extension.

2. The pin detecting system of claim 1 comprising a control which is responsive to at least one of said signals generated by said at least one sensor.

3. The pin detecting system of claim 2, wherein said control is operable to determine a degree of wear in at least one of said pins, the center links and the side links of the section of chain in response to said at least one sensor.

4. The pin detecting system of claim 3, wherein said control is operable to determine said degree of wear in response to at least two signals generated by said at least one sensor which are indicative of the detection of at least two extensions.

5. The pin detecting system of claim 2, wherein said control is operable to control at least one accessory in response to said at least one sensor.

6. The pin detecting system of claim 2, wherein said at least one accessory comprises a lubrication device positioned along the conveying path, said control being operable to activate or deactivate said lubrication device in response to said at least one sensor.

7. The pin detecting system of claim 2, wherein said control is operable to control conveyance of the chain along the conveying path in response to said at least one sensor.

8. The pin detecting system of claim 1, wherein said at least one sensor comprises an optical sensor which detects the presence of said extension as said extension passes said at least one sensor.

9. The pin detecting system of claim 1, wherein said at least one sensor comprises a mechanical trip device which contacts said extension as said extension passes thereby to detect the presence of said extension at said at least one sensor.

10. The pin detecting system of claim 1, wherein said at least one of said plurality of pins comprises at least one of a forged I-pin, a smooth I-pin and a bolt.

11. A method for detecting at least one pin of a section of chain of a conveyor system, said method comprising:

providing a section of chain having a plurality of chain links connected together via a plurality of pins;

providing a detector along a conveying path of the conveyor system; and detecting an end of at least one of said pins with said detector as said pins move along said conveying path, said detector generating a signal indicative of a detection of an end of at least one of said pins.

12. The method of claim 11, wherein detecting said end of said pins comprises detecting a raised projection extending longitudinally from at least one end of said pins.

13. The method of claim 12, wherein detecting a raised projection comprises detecting a generally pointed tip of a raised projection extending longitudinally from at least one end of said pins.

14. The method of claim 11 including controlling at least one accessory associated with the conveyor system in response to said at least one signal generated by said detector.

15. The method of claim 14, wherein controlling at least one accessory comprises activating or deactivating a lubrication device positioned along the conveying path.

16. The method of claim 14, wherein controlling at least one accessory comprises controlling a drive system of the conveyor system.

* * * * *